United States Patent
Breen et al.

(10) Patent No.: US 6,478,948 B2
(45) Date of Patent: Nov. 12, 2002

(54) METHOD OF MONITORING AND CONTROLLING CORROSION OF FURNACE BOILER TUBES

(75) Inventors: Bernard P. Breen, Pittsburgh, PA (US); Dennis Tobias, Pittsburgh, PA (US); David Eden, Old Deer (GB); James E. Gabrielson, Hanover, MN (US); Ralph W. McConnell, Pittsburgh, PA (US)

(73) Assignee: ESA Corrosion Solutions, Ltd., Lawrence, PA (US)

( * ) Notice: Subject to any disclaimer, the term of this patent is extended or adjusted under 35 U.S.C. 154(b) by 66 days.

(21) Appl. No.: 09/793,792

(22) Filed: Feb. 26, 2001

(65) Prior Publication Data

US 2002/0117401 A1 Aug. 29, 2002

(51) Int. Cl.$^7$ ............................................ C23F 13/00
(52) U.S. Cl. .................... 205/740; 205/725; 205/775.5; 205/776; 205/777; 204/196.02; 204/196.06; 204/196.11; 204/196.37; 204/404; 376/249; 376/256; 376/257; 324/71.1; 324/71.2; 324/439; 324/446; 324/448; 110/343; 110/347
(58) Field of Search ........................... 204/196.11, 404, 204/196.02, 196.06, 196.37; 205/740, 775.5, 776, 777, 781, 785.5, 786.5, 793.5; 376/249, 256, 257; 324/71.1, 71.2, 439, 446, 448; 110/343, 347

(56) References Cited

U.S. PATENT DOCUMENTS

| | | | | |
|---|---|---|---|---|
| 2,834,858 A | * | 5/1958 | Schaschl ....................... 201/63 |
| 3,491,012 A | * | 1/1970 | Winslow, Jr. ................ 204/404 |
| 3,504,323 A | * | 3/1970 | Meany, Jr. .................... 338/13 |
| 4,426,618 A | * | 1/1984 | Ronchetti et al. ........ 324/65 CR |
| 4,575,678 A | | 3/1986 | Hladky ........................ 324/425 |
| 4,935,195 A | * | 6/1990 | Palusamy et al. ............ 376/249 |
| 5,139,627 A | | 8/1992 | Eden et al. |
| 5,286,357 A | | 2/1994 | Smart et al. |
| 5,323,429 A | * | 6/1994 | Roarty et al. ................ 376/249 |
| 5,425,867 A | | 6/1995 | Dawson et al. |
| 5,809,913 A | * | 9/1998 | Kramer et al. .............. 110/347 |
| 6,294,074 B1 | * | 9/2001 | Lin et al. .................. 205/777.5 |

FOREIGN PATENT DOCUMENTS

WO     WO 99/42811     8/1999

* cited by examiner

Primary Examiner—Bruce F. Bell
(74) Attorney, Agent, or Firm—Buchanan Ingersoll, P.C.

(57) ABSTRACT

A method for monitoring and reducing corrosion in furnace boiler tubes measures electrochemical noise associated with corrosion mechanisms while corrosion is occurring at the surface of the tubes as they are exposed to combustion products. This noise is detected using a probe at the boiler waterwall surface that is connected to a corrosion monitor. The monitor contains a computer and software which determines a corrosion rate from the measured electrochemical noise. That rate is compared to a standard to determine if the rate is within acceptable limits. If not, the operator of the furnace or an Adaptive Process Controller (APC) is notified and adjusts one or more burners to change the combustion products that are responsible for the corrosion. Such an adjustment could be made by changing the amount of air or fuel being provided to the burner or other air slots or air ports. After that adjustment is made the furnace emissions could be checked for NOx, SOx and particulate emissions and further adjustments could be made to the burners to reduce those emissions.

17 Claims, 2 Drawing Sheets

METHOD OF MONITORING AND CONTROLLING CORROSION OF FURNACE BOILER TUBES

FIELD OF THE INVENTION

The invention relates to a method for determining a rate at which boiler tubes that are exposed to combustion products are corroding and taking steps to reduce the corrosion rate.

BACKGROUND OF THE INVENTION

For many years electricity has been produced using boilers or furnaces which generate steam that drives a turbine. Many of the furnaces used to produce electricity have a series of tubes that run along or form the inside walls of the furnace. One surface of the tubes faces the combustion chamber and is heated. The tubes are usually made from iron containing metal alloys. During operation of the furnace an iron oxide film forms on the fire side surface of the tubes. Ash particles and slag also accumulate on top of the iron oxide film. That slag is a solution or mixture of iron and silicon oxides which is commonly identified as $Fe_xO_ySiO_2$. Other chemicals, particularly calcium may also be present in the slag. Depending upon the relative amounts of calcium, iron and silicon present in the slag, the slag will be either liquid or solid at operating temperatures within the furnace. When the ash is liquid, it is generally referred as fused ash, vitrified ash, or most commonly as slag.

Until recent years furnace boiler tubes corroded slowly and had a service life of 20 to 30 years. However, the introduction of low NOx burners has increased the rate of boiler tube corrosion which can reduce their life expectancy to only 1 to 2 years. The result is that not only do tubes have to be replaced at an expense of $2 to $5 million dollars per boiler (for two complete sidewall panel replacements), but the corrosion problem has also resulted in the need to improve coal quality, sometimes doubling the cost of coal. Consequently, there is a need for a method that will reduce corrosion of furnace boiler tube walls in furnaces fired to low NOx emissions. The water inside boiler tubes is at a high pressure, typically from 2000 to about 5000 psi. Consequently, the tubes could fail if their walls become too thin as a result of corrosion. For this reason, the industry has periodically measured the thickness of the walls of its boiler tubes using sonic measuring techniques and other methods. When these measurements indicate that the walls are becoming too thin, the boiler tubes are replaced. While the industry has been able to determine corrosion rates from periodic measurements of wall thickness, corrosion rates determined in this way are of little use in efforts to control corrosion.

The corrosion of furnace wall tubes involves several mechanisms. First, removal of the protective oxide film allows further oxidation. Second, if the oxide film is not present the iron surface is attacked and pitted by condensed phase chlorides which may be present. A third mechanism occurs when wet slag runs across the surface of the film. As that happens, iron from the tube goes into the slag solution which contains low fusion calcium-iron-silicate eutectics that are formed in the liquid slag under reducing conditions in the furnace. Reduced sulfur in the form of S, $H_2S$, FeS or $FeS_2$ can react with the oxygen of the tube scale depriving the tube metal of its protective layer. If one understood what caused each of the mechanisms to occur and could detect when they are occurring, then steps could be taken to prevent corrosion. Yet, prior to the present invention the art has not done this.

Within the past fifteen years corrosion engineers have developed probes and methods which can monitor corrosion rates in real time as corrosion is occurring in a variety of equipment. These probes and methods are based upon a recognition that corrosion is an electrochemical process during which electrochemical noise is generated. Electrochemical noise is a generic term used to describe low amplitude, low frequency random fluctuations of current and potential observed in electrochemical systems. Thus, by placing electrodes in the corrosive environment, one can measure the electrochemical noise that is present. Hladky in U.S. Pat. No. 4,575,678 discloses that measurements of electrochemical noise can be used to calculate a rate at which corrosion is occurring. He further discloses an apparatus for measuring corrosion that is occurring in a variety of liquid containing apparatus such as pipes, storage tanks, heat exchangers, pumps and valves. Eden et al. discloses a corrosion monitoring apparatus in U.S. Pat. No. 5,139,627 which also relies upon measurements of electrochemical noise. This apparatus has been commercialized by Integrity Solutions of Aberdeen, Scotland, and is being sold under the name MENTOR CORROSION SURVEILLANCE system. These devices have been used to measure corrosion in storage tanks and pipes. However, the art has not realized that they could be used in furnaces where temperatures exceed 2000° F. and where corrosion occurs because of chloride reactions and metal oxidation, sulfation, and reduction reactions within the wet slag.

SUMMARY OF THE INVENTION

We provide a method for monitoring corrosion of furnace boiler tubes by measuring electrochemical noise occurring at the surface of the tubes while that surface is exposed to combustion products. We further provide a method for controlling that corrosion. A probe is provided for measuring electrochemical noise. The probe is connected to a corrosion monitor having a computer and software which determines a corrosion rate from the measured electrochemical noise. That rate is compared to a standard to determine if the rate is within acceptable limits. If not, the operator of the furnace is notified and changes are made to the amount of air or fuel being provided to one or more burners.

Other objects and advantages of the invention will become apparent from a description of certain preferred embodiments shown in the drawings.

DESCRIPTION OF THE PREFERRED EMBODIMENTS

Figure 1:
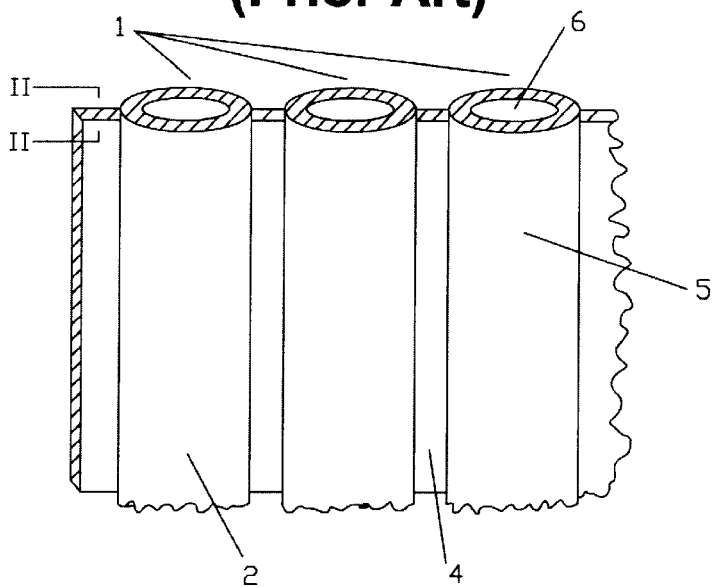
FIG. 1 is a front view of a portion of three boiler tubes.
Figure 2:
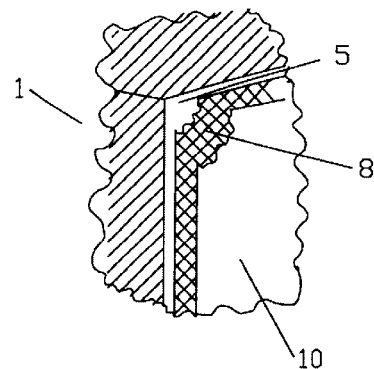
FIG. 2 is a sectional view taken along the line II—II of FIG. 1.

As shown in FIG. 1, a boiler tube wall panel 1 used in furnaces to produce electricity is comprised of a series of tubes 2 connected by webs 4. One surface 5 of the panel 1 faces the interior of the furnace and is exposed to the products of combustion since combustion is occurring within the furnace. This surface 5 is called the fire side. Water flows through the center 6 of the tubes 2 and is heated by the fire side combustion. During manufacture of the boiler tube wall panels an oxide layer 8 is formed on the exposed surfaces of the panel. This oxide layer is present when the panel is installed in the furnace and provides some corrosion protection. During operation of the furnace a slag layer is formed on most of the fire side of the boiler tubes. Thus, the fire side surface 5 of the tubes is coated with a slag 10 that forms on the oxide film 8 as shown in FIG. 2. At any given temperature in the furnace the slag will be liquid or solid depending upon the relative amounts of iron, calcium and silicon in the slag. It is also true that reducing conditions within the boiler can lower the fusion temperature of slag by 150° F. to as much as 300° F., i.e., from 2,300° F. down to 2,150° F. Such reducing conditions are often created when burners are operated in a low NOx firing mode or when low NOx burners are used. Consequently, the slag will become liquid at much lower temperatures. When slag is in a liquid form iron from the boiler tubes easily migrates into the slag resulting in corrosion. Although the final liquid phase of the slag may not be electrochemical, the dissolving and migration of iron into that phase are electrochemical. Thus, the formation of liquid slag gives off electrochemical signals and noise which can be detected. Since corrosion is likely to occur while the slag is in a liquid phase, detection of phase change from solid to liquid is an indicator that corrosion has begun and the migration of iron atoms into the slag solution creates the electrical noise which is a direct measure of the corrosion rate.

A second type of corrosion occurs when the protective oxide layer 8 is removed. This can occur when a reducing atmosphere is present and flame impinges on the surface. This condition can exist during low NOx firing. Removal of the protective oxide film involves a reduction of iron oxide to reduced iron, or iron sulfide. That process is accompanied by generation of electrochemical noise. Such noise can also be detected.

During transition from oxide to reducing skin condition, the iron surface is attacked and pitted by the presence of condensed phase chlorides. These chlorides only attack the iron surface when it is in transition between oxidizing and reducing. The chloride and iron reaction is part of an electrochemical corrosion mechanism which generates noise that can be detected.

Figure 3:
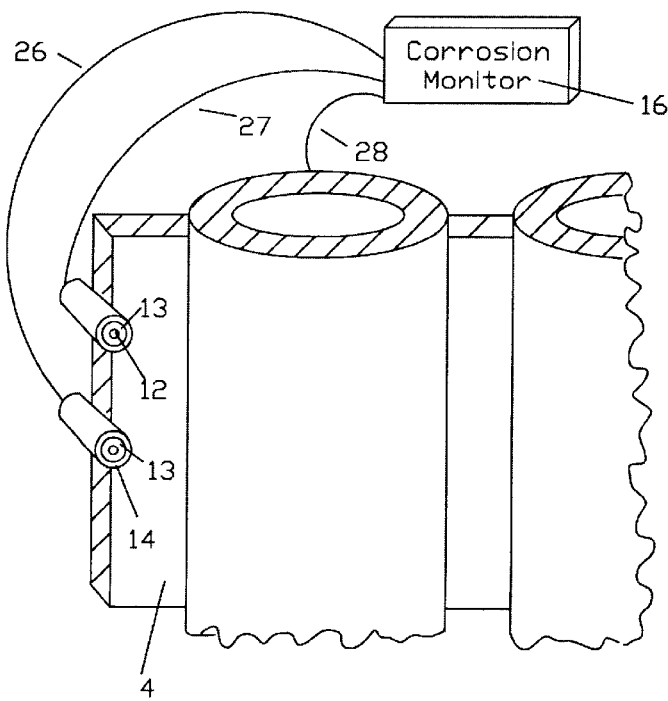
FIG. 3 is a view similar to FIG. 1 showing a first present preferred embodiment of a probe useful to practice our method.
Figure 4:
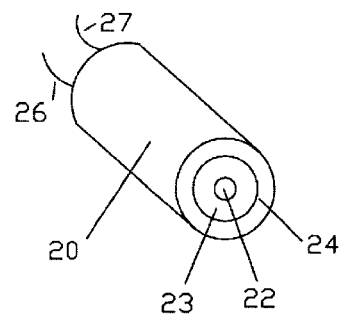
FIG. 4 is a perspective view of a second present preferred probe.
Figure 5:
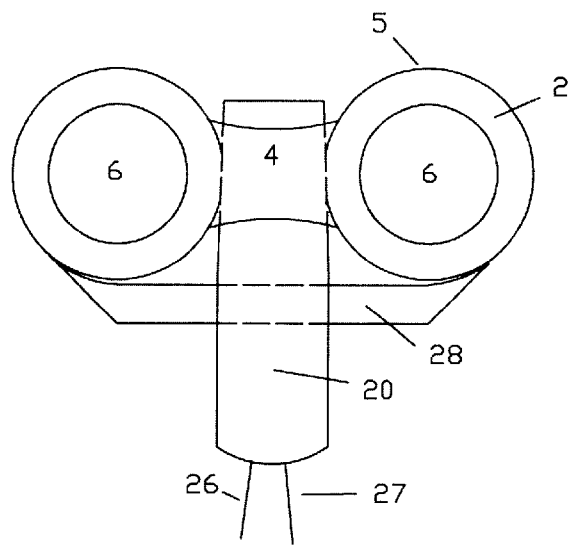
FIG. 5 is a top plan view of a portion of a furnace boiler tube wall with the probe of FIG. 4 installed.

Since the corrosion mechanisms that occur on furnace boiler tubes are accompanied by noise, we provide a probe to monitor the tube surface and detect that noise. The monitor will include two spaced apart electrodes 12 and 14 each surrounded by an insulator 13 on the surface of the tube. As shown in FIG. 3, we prefer that the electrodes extend through the web 4 of the panel. The electrodes are connected to a corrosion monitor 16. The monitor 16 converts electrochemical noise detected by the electrodes 12, 14 into a corrosion rate. The technique is described in U.S. Pat. No. 4,575,678 to Hladkey and U.S. Pat. No. 5,139,627 to Eden et al. A corrosion monitor available from Integriti Solutions and under the name MENTOR CORROSION SURVEILLANCE system could be used. Another probe 20 that could be used is a tube shown in FIGS. 4 and 5. The probe 20 has a center electrode 22 surrounded by an insulator 23 and a second electrode 24. We prefer that the probe 20 be supported by bracket 28 and extend through the web 4 as shown in FIG. 5. The top of the probe 20 should be close enough to the surface of the web 4 so that the probe tip is at a temperature that is close to or the same as the temperature of the 5 of the tube wall. The probe can project into the furnace a distance of ⅛" to ¼". The probe is connected to a corrosion monitoring system by wires 26 and 27. The wires can be copper, the electrodes preferably are of the same material as the tube surface and the insulator can be a titanium oxide material.

Figure 6:
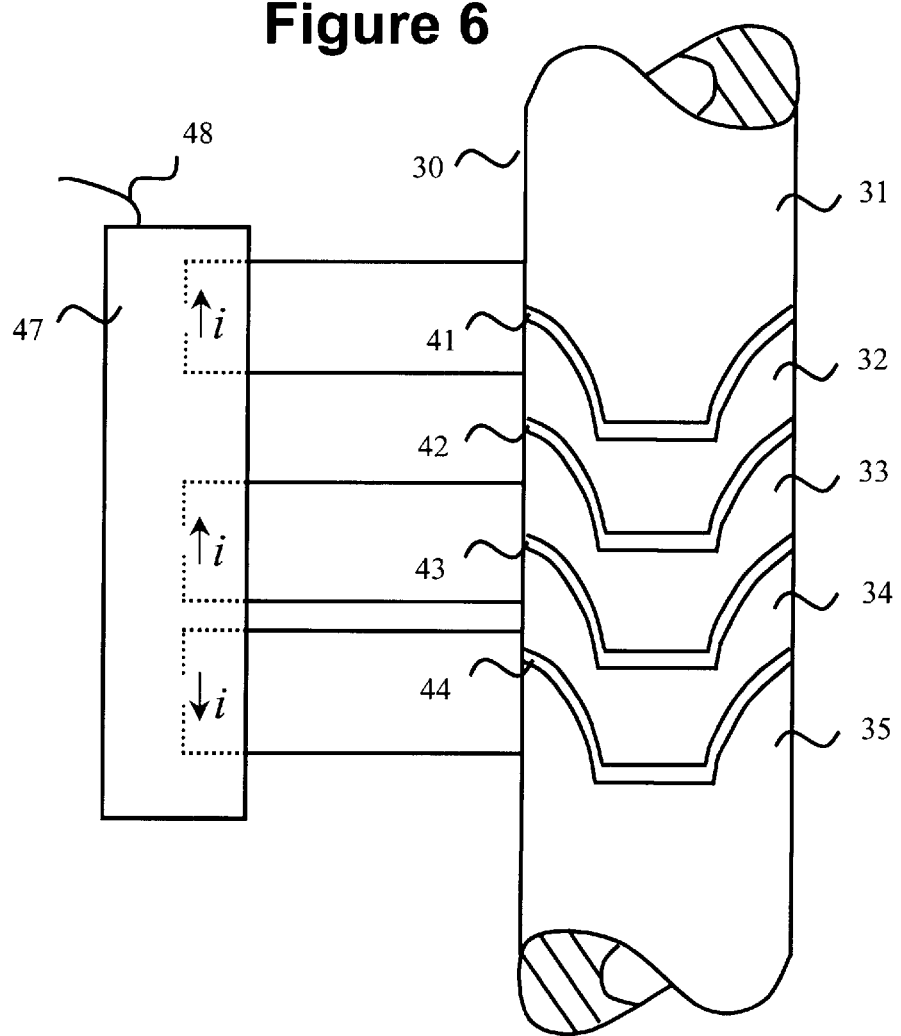
FIG. 6 is a perspective view of a third preferred probe.

In another preferred embodiment shown in FIG. 6 the probe is fabricated as part of a boiler tube. This tube 30 has an upper portion 31 and lower portion 35 between which there are three or more intermediate sections 32, 33 and 34 separated by insulators 41, 42, 43 and 44. The insulators prevent current flow between adjacent sections. A wire 46 is connected between each section and a detector 47 capable of measuring current, i. The detector could be a simple voltage meter When slag forms on the fireside surface of the tube, the slag can conduct electricity. Consequently, any electrochemical activity in the slag will generate detectable current flowing through wires 46. The detector 47 is connected to a corrosion monitor (not shown) by cable 48. The corrosion monitor translates the detected current to measurements of corrosion occurring on the surface of the tube.

The probe and corrosion monitor provide the furnace operator with real time information about when corrosion is occurring. That information can be correlated to several operating conditions such as burner air register settings, slot register settings fan settings, fuel consumption and other factors. We have observed that corrosion rates are higher when reducing conditions exist in the furnace. One can change these conditions by changing the air flow into the furnace. By correlating burner air register or slot air register settings (when available) with corrosion rate data, a profile can be used to identify operating conditions of individual burners which are conducive to increased corrosion rates. Then, these operating conditions can be avoided.

Even if no profile exists or can be developed, information on corrosion rates is still useful. The operator can compare the detected corrosion rate to a tube life standard.

Boiler tubes are considered to be exhausted when the thickness of the tube wall reaches a specific thickness. That may be different for boiler tubes of different alloy compositions. Nevertheless, it is a simple matter to establish an acceptable corrosion rate for a given boiler tube by dividing the difference between the initial tube wall thickness and the minimum acceptable tube wall thickness by the desired tube life in years. If the observed corrosion rate is greater than the acceptable corrosion rate, the furnace operator can change the burner settings to reduce the corrosion rate even when protective or sacrificial cladding is used.

It should be noted that changing burner settings could change the amount of NOx, SOx and particulates exiting the combustion chamber. Consequently, the furnace operator or adaptive control software sometimes called an Adaptive Process Controller or APC which controls the furnace should also look at the monitors which measure these emissions or conduct emission tests after changing the burner settings. For a particular furnace, it may be necessary to induce a higher than desirable corrosion rate of the furnace boiler tubes to meet desired emission levels. Thus, in one embodiment of our method the furnace operator or APC monitors corrosion rates, compares each observed rate to a standard, checks emission levels, adjusts at least one burner and then checks emission levels again. The second emissions check may prompt the operator or APC to make further burner adjustments to reduce emissions. That adjustment could change corrosion rates, but, will determine the most effective NOx control operating conditions.

Furnaces which have boiler tubes typically have more than one burner. Consequently, several burners could be adjusted in response to an observed corrosion rate.

Although we have illustrated a single probe in a boiler wall, we expect that furnace owners would install several such probes throughout the furnace boiler tube wall panels. This would be done because conditions within the furnace vary. A reducing atmosphere could be present in one region of the furnace, but not be present in other regions. Having several probes enables the furnace operator or APC to determine if a particular burner has a greater effect upon corrosion occurring at a particular location. With that knowledge the operator or APC could adjust only that burner or operate that burner in a manner to reduce corrosion while generating more NOx emissions and at the same time adjust another burner to compensate for the increased NOx. Similarly, should an adjustment to a burner to reduce corrosion result in increased NOx emissions, the furnace operator or APC may be able to adjust reburn injectors in the upper furnace to remove more NOx and SOx. This technique is well-known in the art. Examples of such reburn methods are disclosed in U.S. Pat. Nos. 6,030,204; 5,746,144; 5,078,064 and 5,181,475.

We have here described certain present preferred embodiments of our method and monitor for monitoring and reducing emissions of boiler tube panels. However, it should be distinctly understood that our invention is not limited thereto, but may be variously embodied within the scope of the following claims.

We claim:

1. A method of controlling furnace boiler tube corrosion wherein the boiler tubes have a fire side that is exposed to products of combustion which creates electrochemical noise at the fire side surface, the tubes being in a furnace having burners to which fuel and air are provided comprising:
   a. attaching a probe to the interior side of the boiler tubes, the probe capable of measuring electrochemical noise occurring in an electrochemical system;
   b. monitoring the electrochemical noise occurring at the fire side surface of the boiler tubes;
   c. determining from the monitoring of the electrochemical noise a corrosion rate that is occurring at the fire side surface of the boiler tubes;
   d. deciding if the corrosion rate is acceptable; and
   e. if the corrosion rate is not acceptable, adjusting at least one of the fuel and air that is being provided to at least one of the burners.

2. The method of claim 1 wherein the probe is comprised of at least two spaced apart electrodes.

3. The method of claim 1 wherein the probe is comprised of a first electrode and a second electrode encircling the first electrode.

4. The method of claim 1 wherein the boiler tubes have a web portion and the probe extends through the web portion.

5. The method of claim 1 also comprising the steps of measuring NOx emissions from the furnace before and after adjusting at least one of the fuel and air that is being provided to at least one of the burners.

6. The method of claim 1 also comprising the step of adjusting at least one fuel injector in an upper portion of the furnace.

7. The method of claim 6 also comprising the step of measuring emissions of at least one of NOx, SOx and particulates after adjusting the at least one fuel injector.

8. The method of claim 1 also comprising the steps of measuring omissions of at least one of NOx, SOx and particulates after adjusting the burner and then again adjusting that burner.

9. The method of claim 1 also comprising the step of measuring at least one of NOx, SOx and particulates after the adjusting step and then adjusting at least one of the fuel and air that is being provided to a second burner.

10. An improved furnace boiler tube panel of the type having a plurality of tubes interconnected by webs wherein the improvement comprises means for measuring electrochemical noise attached to at least one of the webs and the tubes.

11. The improved furnace boiler tube of claim 10 wherein the measuring means is comprised of at least two spaced apart electrodes connected to a corrosion monitor.

12. The improved furnace boiler tube panel of claim 11 wherein at least one of the electrodes extends through a web.

13. The improved furnace boiler tube of claim 11 wherein the at least two spaced apart electrodes is comprised of a first electrode, an insulator surrounding the first electrode and a second electrode encircling the first electrode and the insulator.

14. The improved furnace boiler tube panel of claim 13 wherein the insulator is comprised of titanium oxide.

15. The improved furnace boiler tube panel of claim 14 also comprising at least one current detector connected to adjacent tube sections.

16. The improved furnace boiler tube panel of claim 15 also comprising a corrosion monitor connected to at least one detector.

17. The improved furnace boiler tube panel of claim 10 wherein a portion of at least one of the tubes contains a plurality of the tube sections and insulators separating adjacent tube sections.

\* \* \* \* \*